United States Patent
McIntosh

(10) Patent No.: US 7,462,188 B2
(45) Date of Patent: Dec. 9, 2008

(54) DEVICE AND METHOD FOR SUTURING INTRACARDIAC DEFECTS

(75) Inventor: Scott A. McIntosh, Sunnyvale, CA (US)

(73) Assignee: Abbott Laboratories, Abbott Park, IL (US)

( * ) Notice: Subject to any disclaimer, the term of this patent is extended or adjusted under 35 U.S.C. 154(b) by 500 days.

(21) Appl. No.: 10/948,445

(22) Filed: Sep. 22, 2004

(65) Prior Publication Data

US 2005/0070923 A1    Mar. 31, 2005

Related U.S. Application Data

(60) Provisional application No. 60/540,811, filed on Jan. 30, 2004, provisional application No. 60/506,536, filed on Sep. 26, 2003.

(51) Int. Cl.
*A61B 17/06* (2006.01)
*A61B 17/04* (2006.01)

(52) U.S. Cl. .................................. 606/213; 606/144

(58) Field of Classification Search ............... 606/139, 606/144–150, 213–217, 222, 228–232; 128/898, 128/899, 897
See application file for complete search history.

(56) References Cited

U.S. PATENT DOCUMENTS

| | | |
|---|---|---|
| 312,408 A | 2/1885 | Wackerhagen |
| 659,422 A | 10/1900 | Shidler |
| 2,012,776 A | 8/1935 | Roeder |
| 2,127,903 A | 8/1938 | Bowen |
| 2,397,823 A | 4/1946 | Walter |

(Continued)

FOREIGN PATENT DOCUMENTS

DE    912619    5/1991

(Continued)

OTHER PUBLICATIONS

U.S. Appl. No. 09/651,344, filed Aug. 29, 2000.

(Continued)

*Primary Examiner*—Todd E Manahan
*Assistant Examiner*—Kathleen Sonnett
(74) *Attorney, Agent, or Firm*—Fulwider Patton LLP

(57) ABSTRACT

In accordance with the present invention there is provided a suturing device. The suturing device includes a length of suture that will be delivered to the site of the PFO and placed through the tissue adjacent the opening to close the PFO. As described in greater detail below, the suture is advanced through the tissue surrounding the opening by a pair of needles that penetrate the tissue adjacent to the opening. A knot is then loosely tied with the length of suture and advanced to the site of the PFO. The tails of the suture extending from the knot are then cut and removed. It is also contemplated that a pre-formed or pre-tied knot may be disposed on the device, wherein after deployment of the suture through the tissue adjacent to the PFO and removal of the device a loop of suture having a pre-tied knot will remain, wherein the pre-tied knot may then be tightened to close the PFO. Further still it is contemplated that other means may be utilized to retain the sutures. For example, it is contemplated that a suture clip or other clip like device may be utilized to retain the suture in a position such that the PFO is closed.

15 Claims, 7 Drawing Sheets

U.S. PATENT DOCUMENTS

Figure 3:
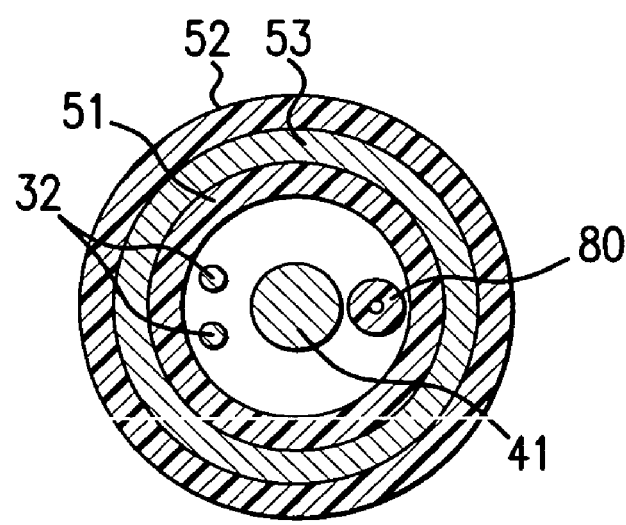

| | | |
|---|---|---|
| RE22,857 E | 3/1947 | Ogburn |
| 2,646,045 A | 7/1953 | Priestley |
| 2,941,489 A | 6/1960 | Fischbein |
| 2,959,172 A | 11/1960 | Held |
| 3,104,666 A | 9/1963 | Hale et al. |
| 3,197,102 A | 7/1965 | Bates et al. |
| 3,422,181 A | 1/1969 | Chirgwin, Jr. |
| 3,470,875 A | 10/1969 | Johnson |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,820,544 A | 6/1974 | Semm |
| 3,840,017 A | 10/1974 | Violante |
| 3,874,388 A | 4/1975 | King et al. |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,109,658 A | 8/1978 | Hughes |
| 4,161,951 A | 7/1979 | Scanlan, Jr. |
| 4,168,073 A | 9/1979 | LaRue |
| 4,182,339 A | 1/1980 | Hardy, Jr. |
| 4,216,776 A | 8/1980 | Downie et al. |
| 4,235,177 A | 11/1980 | Arbuckle |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,493,323 A | 1/1985 | Albright et al. |
| 4,553,543 A | 11/1985 | Amarasinghe |
| 4,587,969 A | 5/1986 | Gillis |
| 4,596,559 A | 6/1986 | Fleishhacker |
| 4,629,450 A | 12/1986 | Suzuki et al. |
| 4,651,733 A | 3/1987 | Mobin-Uddin |
| 4,723,549 A | 2/1988 | Wholey et al. |
| 4,738,666 A | 4/1988 | Fuqua |
| 4,744,364 A | 5/1988 | Kensey |
| 4,803,984 A | 2/1989 | Narayanan et al. |
| 4,836,205 A | 6/1989 | Barrett |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,078,721 A | 1/1992 | McKeating |
| 5,080,664 A | 1/1992 | Jain |
| 5,100,419 A | 3/1992 | Ehlers |
| 5,100,432 A | 3/1992 | Matsutani |
| 5,109,780 A | 5/1992 | Slouf et al. |
| 5,129,912 A | 7/1992 | Noda et al. |
| 5,129,913 A | 7/1992 | Ruppert |
| 5,147,373 A | 9/1992 | Ferzli |
| 5,156,788 A | 10/1992 | Chesterfield et al. |
| 5,160,339 A | 11/1992 | Chen et al. |
| 5,171,251 A | 12/1992 | Bregen et al. |
| 5,178,629 A | 1/1993 | Kammerer |
| 5,192,294 A | 3/1993 | Blake, III |
| 5,192,302 A | 3/1993 | Kensey et al. |
| 5,211,650 A | 5/1993 | Noda et al. |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,242,427 A | 9/1993 | Bilweis |
| 5,250,033 A | 10/1993 | Evans et al. |
| 5,250,053 A | 10/1993 | Snyder |
| 5,254,126 A | 10/1993 | Filipi et al. |
| 5,258,003 A | 11/1993 | Ciaglia et al. |
| 5,259,846 A | 11/1993 | Granger et al. |
| 5,279,311 A | 1/1994 | Snyder |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | Van Tassel et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,354,312 A | 10/1994 | Brinkerhoff et al. |
| 5,364,408 A | 11/1994 | Gordon |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,387,221 A | 2/1995 | Bisgaard |
| 5,387,227 A | 2/1995 | Grice |
| 5,391,176 A | 2/1995 | de la Torre |
| 5,395,332 A | 3/1995 | Ressemann et al. |
| 5,395,349 A | 3/1995 | Quiachon et al. |
| 5,397,325 A | 3/1995 | Delia Badia et al. |
| 5,403,329 A | 4/1995 | Hinchcliffe |
| 5,403,338 A | 4/1995 | Milo |
| 5,411,481 A | 5/1995 | Allen et al. |
| 5,413,571 A | 5/1995 | Katsaros et al. |
| 5,417,699 A | 5/1995 | Klein et al. |
| 5,425,705 A | 6/1995 | Evard et al. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,470,338 A | 11/1995 | Whitfield et al. |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |

| | | | | | | |
|---|---|---|---|---|---|---|
| 5,489,295 A | 2/1996 | Piplani et al. | | 5,897,564 A | 4/1999 | Schulze et al. |
| 5,496,332 A | 3/1996 | Sierra et al. | | 5,902,311 A | 5/1999 | Andreas et al. |
| 5,507,744 A | 4/1996 | Tay et al. | | 5,904,697 A | 5/1999 | Gifford, III et al. |
| 5,507,755 A | 4/1996 | Gresl et al. | | 5,928,266 A | 7/1999 | Kontos |
| 5,507,757 A | 4/1996 | Sauer et al. | | 5,951,590 A | 9/1999 | Goldfarb |
| 5,507,758 A | 4/1996 | Thomason et al. | | 5,954,732 A | 9/1999 | Hart et al. |
| 5,509,902 A | 4/1996 | Raulerson | | 5,957,937 A | 9/1999 | Yoon |
| 5,520,665 A | 5/1996 | Fleetwood | | 6,024,747 A | 2/2000 | Kontos |
| 5,520,691 A * | 5/1996 | Branch ........................ 606/72 | | 6,036,699 A | 3/2000 | Andreas et al. |
| 5,520,702 A | 5/1996 | Sauer et al. | | 6,042,601 A | 3/2000 | Smith |
| 5,527,321 A | 6/1996 | Hinchliffe | | 6,048,351 A | 4/2000 | Gordon et al. |
| 5,527,322 A | 6/1996 | Klein et al. | | 6,048,354 A | 4/2000 | Lawrence |
| D372,310 S | 7/1996 | Harnett | | 6,117,144 A | 9/2000 | Nobles et al. |
| 5,531,700 A | 7/1996 | Moore et al. | | 6,136,010 A * | 10/2000 | Modesitt et al. ............. 606/144 |
| 5,536,273 A | 7/1996 | Lehrer | | 6,245,079 B1 | 6/2001 | Nobles et al. |
| 5,540,701 A | 7/1996 | Sharkey et al. | | 6,436,109 B1 | 8/2002 | Kontos |
| 5,540,704 A | 7/1996 | Gordon et al. | | 6,451,031 B1 | 9/2002 | Kontos |
| 5,545,171 A | 8/1996 | Sharkey et al. | | 6,517,553 B2 | 2/2003 | Klein et al. |
| 5,545,178 A | 8/1996 | Kensey et al. | | 6,562,052 B2 * | 5/2003 | Nobles et al. ................ 606/144 |
| 5,545,180 A | 8/1996 | Le et al. | | 6,641,592 B1 | 11/2003 | Sauer et al. |
| 5,549,618 A | 8/1996 | Fleenor et al. | | 6,716,228 B2 | 4/2004 | Tal |
| 5,554,162 A | 9/1996 | DeLange | | 2002/0177876 A1 | 11/2002 | Roby et al. |
| 5,562,684 A | 10/1996 | Kammerer | | 2003/0093093 A1 | 5/2003 | Modesitt et al. |
| 5,562,686 A * | 10/1996 | Sauer et al. ................ 606/144 | | 2004/0122449 A1 | 6/2004 | Modesitt |
| 5,562,688 A | 10/1996 | Riza | | 2004/0210251 A1 | 10/2004 | Kontos |
| 5,562,728 A | 10/1996 | Lazarus et al. | | 2004/0225301 A1 | 11/2004 | Roop et al. |
| 5,569,271 A | 10/1996 | Hoel | | 2005/0143761 A1 | 6/2005 | Modesitt |
| 5,573,540 A | 11/1996 | Yoon | | 2006/0079914 A1 | 4/2006 | Modesitt |
| 5,591,177 A | 1/1997 | Lehrer | | 2006/0142785 A1 | 6/2006 | Modesitt |
| 5,591,179 A | 1/1997 | Edelstein | | 2007/0167959 A1 | 7/2007 | Modesitt |
| 5,591,206 A | 1/1997 | Moufarrege | | | | |
| 5,593,421 A | 1/1997 | Bauer | | FOREIGN PATENT DOCUMENTS | | |
| 5,603,718 A | 2/1997 | Xu | | | | |
| 5,609,597 A | 3/1997 | Lehrer | | DE | 4220283 | 6/1992 |
| 5,611,794 A | 3/1997 | Sauer et al. | | DE | 4210724 C1 | 7/1993 |
| 5,613,974 A | 3/1997 | Andreas et al. | | DE | 9217932 U1 | 7/1993 |
| 5,613,975 A | 3/1997 | Christy | | EP | 0 140 557 | 5/1985 |
| 5,643,289 A | 7/1997 | Sauer et al. | | EP | 0 207 545 | 1/1987 |
| 5,643,295 A | 7/1997 | Yoon | | EP | 0 474 887 | 3/1992 |
| 5,662,664 A | 9/1997 | Gordon et al. | | EP | 0 478 358 | 4/1992 |
| 5,669,917 A | 9/1997 | Sauer et al. | | EP | 0 589 409 | 9/1992 |
| 5,676,689 A | 10/1997 | Kensey et al. | | EP | 0 624 343 | 4/1993 |
| 5,700,273 A | 12/1997 | Buelna et al. | | EP | 0 542 126 | 5/1993 |
| 5,707,379 A | 1/1998 | Fleenor et al. | | EP | 0 568 098 | 11/1993 |
| 5,713,910 A | 2/1998 | Gordon et al. | | EP | 0 669 101 | 8/1995 |
| 5,716,369 A | 2/1998 | Riza | | EP | 0 669 102 | 8/1995 |
| 5,720,757 A | 2/1998 | Hathaway et al. | | EP | 0 669 103 | 8/1995 |
| 5,725,552 A | 3/1998 | Kotula et al. | | EP | 0 941 698 | 9/1999 |
| 5,728,109 A | 3/1998 | Schulze et al. | | FR | 105954 | 3/1954 |
| 5,728,114 A | 3/1998 | Evans et al. | | JP | 2119866 A | 5/1990 |
| 5,728,151 A | 3/1998 | Garrison et al. | | JP | 542161 A | 2/1993 |
| 5,741,276 A | 4/1998 | Poloyko et al. | | SU | 993922 | 2/1983 |
| 5,741,280 A | 4/1998 | Fleenor | | SU | 1093329 | 5/1984 |
| 5,749,890 A | 5/1998 | Shaknovich | | SU | 1174036 | 8/1985 |
| 5,759,188 A | 6/1998 | Yoon | | SU | 1544383 | 2/1990 |
| 5,766,183 A | 6/1998 | Sauer | | SU | 1648400 | 5/1991 |
| 5,766,186 A | 6/1998 | Faraz et al. | | SU | 820810 | 6/1997 |
| 5,769,862 A | 6/1998 | Kammerer et al. | | WO | WO 94/05213 | 3/1994 |
| 5,779,719 A | 7/1998 | Klein et al. | | WO | WO 94/27503 | 12/1994 |
| 5,792,151 A | 8/1998 | Heck et al. | | WO | WO 94/28801 | 12/1994 |
| 5,799,661 A | 9/1998 | Boyd et al. | | WO | WO 95/05121 | 2/1995 |
| 5,810,849 A * | 9/1998 | Kontos ........................ 606/144 | | WO | WO 95/35065 | 12/1995 |
| 5,810,850 A | 9/1998 | Hathaway et al. | | WO | WO 97/03613 | 2/1997 |
| 5,817,113 A | 10/1998 | Gifford, III et al. | | WO | WO 97/10764 | 3/1997 |
| 5,820,631 A | 10/1998 | Nobles | | WO | WO 97/13461 | 5/1997 |
| 5,824,010 A | 10/1998 | McDonald | | WO | WO 97/17901 | 5/1997 |
| 5,836,955 A | 11/1998 | Buelna et al. | | WO | WO 97/20505 | 6/1997 |
| 5,836,956 A | 11/1998 | Buelna et al. | | WO | WO 00/12013 | 3/2000 |
| 5,846,253 A | 12/1998 | Buelna et al. | | WO | WO 00/51498 | 9/2000 |
| 5,860,990 A | 1/1999 | Nobles et al. | | WO | WO 03/099134 | 4/2003 |
| 5,860,991 A | 1/1999 | Klein et al. | | WO | WO 2005/023119 | 3/2005 |
| 5,871,490 A | 2/1999 | Schulze et al. | | | | |
| 5,871,502 A | 2/1999 | Suryadevara | | | | |

| | | | |
|---|---|---|---|
| WO | WO 2005/025430 | 3/2005 | |

OTHER PUBLICATIONS

U.S. Appl. No. 10/152,272, filed May 20, 2002.
U.S. Appl. No. 10/357,984, filed Feb. 4, 2003.
U.S. Appl. No. 10/652,182, filed Aug. 29, 2003.
U.S. Appl. No. 10/660,288, filed Sep. 11, 2003.
Elgin National Watch Company, Product Brochure entitled Elgiloy®, A Cobalt Nickel Spring.
Faulkner, Catherine B., Letter regarding "VasoSeal Vascular Hemostasis," *Datascope*, New Laurus Medical Corporation,"Endoscopic Suturing Made Simple," The Laurus ND-2600 Needle Driver.
Taber's Cyclopedic Medical Dictionary, 18th Ed., p. 747 (1997).
Marshall, A.C. & Lock, J.E.; "Structural and compliant anatomy of the patent foramen ovale in patients undergoing transcatheter closure", *Am. Heart Journ.*, 140(2):303-307 (2000).
Product Brochure, Laurus Medical Corporation, Irvine, CA "The Laurus In-Line Endoscopic Suturing Device" (Oct. 1994) 1 page.
Rema-Medizintcchnik GmbH, Product Brochure entitled "REMA," 7 pages.
U.S. Appl. No. 90/006,469, filed Nov. 29, 2002, Modesitt.
U.S. Appl. No. 10/357,984, filed Feb. 4, 2003, Modesett et al.
U.S. Appl. No. 11/465,527, filed Aug. 18, 2006, Dawn Ma.
U.S. Appl. No. 11/891,358, filed Aug. 9, 2007.
U.S. Appl. No. 11/891,513, filed Aug. 9, 2007.
6,136,010, Office Action, Mar. 29, 2000.
6,136,010, Notice of Allowance, May 30, 2000.
6,136,010, Issue Notification, Oct. 6, 2000.
6,964,668, Office Action, Jan. 24, 2005.
6,964,668, Notice of Allowance, May 13, 2005.
6,964,668, Issue Notification, Oct. 26, 2005.
7,001,400, Office Action, Feb. 28, 2003.
7,001,400, Office Action, Nov. 7, 2003.
7,001,400, Notice of Allowance, Apr. 20, 2004.
7,001,400, Issue Notification, Feb. 1, 2006.
7,235,087, Office Action, Aug. 9, 2006.
7,235,087, Notice of Allowance, Feb. 22, 2007.
7,235,087, Issue Notification, Jun. 8, 2007.
2004/00092964, Office Action, Jan. 9, 2006.
2004/00092964, Office Action, Mar. 16, 2006.
2004/00092964, Office Action, Sep. 28, 2006.
2004/00092964, Office Action, Mar. 23, 2007.
2004/0122449, Office Action, Dec. 12, 2006.
2004/0122449, Office Action, Jun. 18, 2007.
2005/0059982, Office Action, Nov. 15, 2005.
2005/0059982, Office Action, Mar. 9, 2006.
2005/0059982, Office Action, Aug. 24, 2006.
2005/0059982, Office Action, Feb. 1, 2007.
2005/0059982, Office Action, Jun. 28, 2007.
2005/0143761, Office Action, Apr. 4, 2007.
2006/0079914, Office Action, Jun. 14, 2007.
2006/0142785, Office Action, Jun. 22, 2007.

* cited by examiner

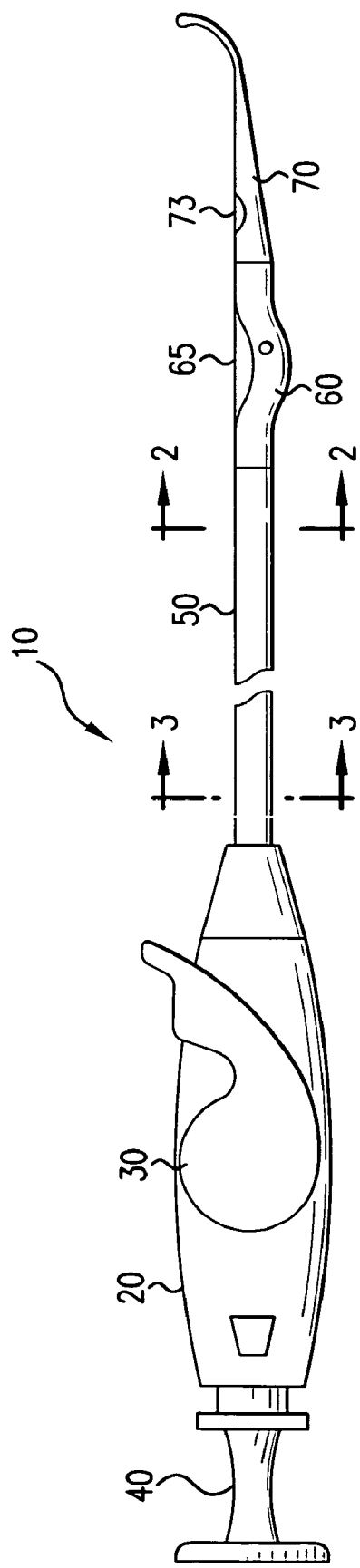
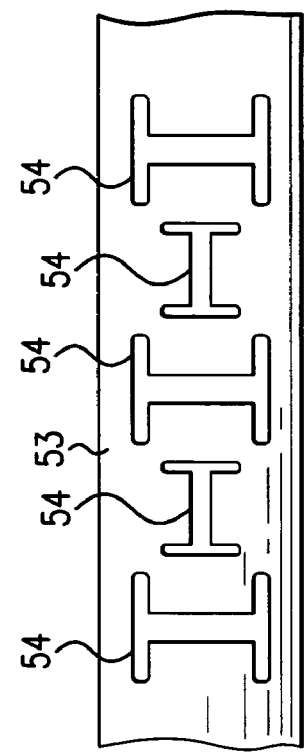
FIG.1
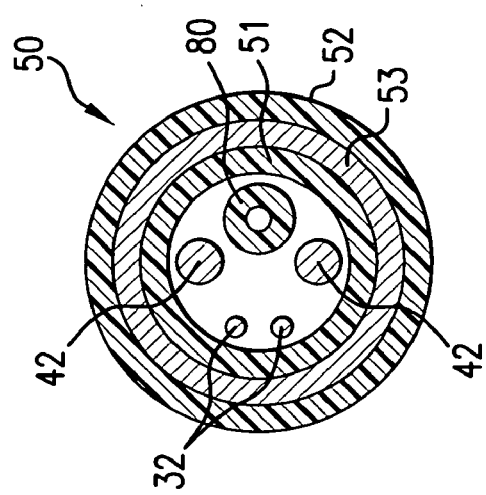
FIG.2a
FIG.2b

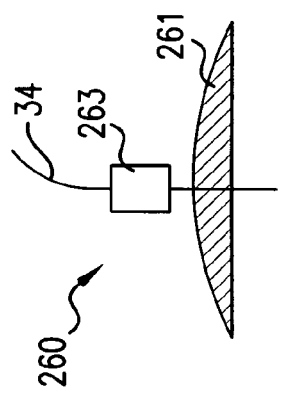
FIG.6b
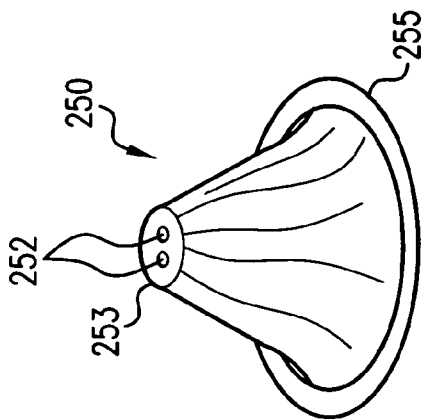
FIG.6d
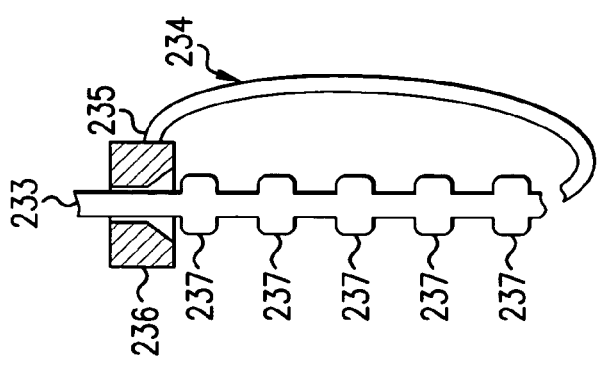
FIG.6a
FIG.6c

DEVICE AND METHOD FOR SUTURING INTRACARDIAC DEFECTS

PRIORITY CLAIM

The present application claims priority to the following U.S. Provisional Patent applications having Ser. No. 60/506,536 and 60/540,811 filed on Sep. 26, 2003 and Jan. 30, 2004 the entireties of which are herein incorporated by reference.

RELATED APPLICATIONS

This application is related to the following U.S. patent applications:
Application Ser. No. 10/660,288, filed Sep. 11, 2003;
Application Ser. No. 10/652,182, filed Aug. 29, 2003;
Application Ser. No. 10/357,984, filed Feb. 4, 2003;
Application Ser. No. 10/152,272, filed May 20, 2002;
Application Ser. No. 09/651,344, filed Aug. 29, 2000; and
application Ser. No. 09/262,402, filed on Mar. 4, 1999, now U.S. Pat. No. 6,136,010.

The disclosures of application Ser. No. 10/660,288, filed Sep. 11, 2003; application Ser. No. 10/652,182, filed Aug. 29, 2003; application Ser. Nos. 09/651,344, 10/152,272, and 10/357,984, as well as U.S. Pat. No. 6,136,010 are hereby incorporated by reference in their entirety.

TECHNICAL FIELD

The present invention relates generally to devices and methods for suturing intracardiac defects, and more particularly, to transcatheter devices and methods for suturing of an intracardiac defect such as a patent foramen ovale.

BACKGROUND OF THE INVENTION

The foramen ovale is an opening between the two aria of the fetal heart. It usually closes shortly after birth as a result of hemodynamic changes related to respiration. If it remains open, or "patent," the defect can be repaired surgically. Taber's Cyclopedic Medical Dictionary, 18.sup.th Ed., 1997, p. 747.

As association has been found between PFO and cryptogenic stroke in patients younger than sixty five (65) years old that suggests that PFO allowing paradoxic embolus may be responsible for stroke when other causes cannot be identified. Id. It has been theorized that closing the patent foramen ovale may be beneficial in reducing incidence of stroke or transient ischemic attacks (TIA) in patients with PFO.

The Devices and methods for transcatheter-based repair of atrial septal defects (ASD) and patent foramina ovalia (PFO) have been developed. The design of such transcatheter devices is largely driven by the structure of the intracardiac and intravascular anatomy. ASDs are relatively simpler lesions, being generally circular or oval shaped defects within a relatively thin septum. Marchall A. C., Lock J. E., Structural and Compliant Anatomy of the Patent Foramen Ovale in Patients Undergoing Transcatheter Closure, Am Heart J August 2000; 140(2);303-7. The anatomical structural features of PFO's, however, are more complex. Id. "he PFO involves two components, septum primum and septum secundum. Septum secundum is thicker than septum primum and exhibits limited mobility and compliance. The failure of these two structures to fuse creates a tunnel-like opening, the PFO. The extent to which these two components of the atrial septum overlap determines the length of this tunnel. The distance of the nonfusion between the septa, when viewed from the left atrial surface, determines its breadth. This later measure ultimately limits the potential size of the PFO. These unique characteristics, which distinguish the PFO from the ASD, should be considered in the design of a device targeted specifically at PFOs." .Id.

"Initial attempts to accommodate the unique anatomy of the PFO yielded devices composed of a pair of offset discs set apart by a relatively long central section. This section theoretically allowed for the length and angulation of the PFO tunnel. The long central section, however, increased bulkiness of the device. Furthermore, we subsequently observed that the central body of the double disc device actually displaced the relatively compliant septum primum, thus shortening the length of the PFO tunnel. After device placement, the long central pin unnecessarily increased the device profile in the heart, thus potentially preventing complete endothelialization. Any relatively rigid device that failed to anticipate changes in the topography of the atrial septum could have similar drawbacks. Thus placement of a device designed for the static rather than the compliant anatomy of the atrial septum could fail to meet the needs of patients with PFO and a history of cryptogenic stroke." Id.

"Transcatheter closure devices have been used to treat lesions as diverse as ASD, ventricular septal defect, and PFO despite the fact that most of these devices were originally designed to close the simple ASD. Ventricular septal defects clearly present challenging substrates for closure devices, often with irregularly configured defect in a thick, muscular septum. Perhaps less well-recognized is the fact that the PFO also poses a unique challenge based on anatomic characteristics of septum secundum, septum primum, and the dynamic relation between the two." Id.

Atrial septal defects have been initially corrected by open heart surgery which required the surgeon to open the chest of a patient and bypass the heart temporarily (eg by means of a heat-lung machine and moderate hypothermia). The surgeon would then physically cut into the heart and suture small defects closed. In the case of larger defects, a patch of biologically compatible material would be sewn onto the septum to cover the defect.

In order to avoid the morbidity, mortality and long recovery times associated with open heart surgery, a variety of transcatheter closure techniques have been invented. In such techniques an occluding device is delivered to the defect site. Once the occluding device is in position it is deployed, wherein many of these devices are configured to be retained within the defect through the use of tension forces, spring force, clips or similar technology. Examples of such occluding devices can be seen in U.S. Pat. Nos. 3,874,388; 4,917,089; 5,725,552; and 5,334,217, wherein these devices are configured to be delivered to the defect in an unexpanded state and then be deployed or opened to seal the defect.

The prior art devices of the above-referenced patents each have their own shortcomings. For example, many of the devices require complex loading devices for delivery of the device to the defect. Additionally, many of the devices require time consuming positioning and deployment procedures which have a high margin for error. Still further, many of the devices require extensive remote manipulation to anchor or deploy the device, this not only increases the amount of time required to deploy the device but also increases the likelihood of errors during deployment.

In addition to those shortcomings mentioned above, another shortcoming is that many of the devices have a geometry which tends to prevent the device from remaining flat against, or within the defect once deployed. Lastly, each of the devices in their expanded and deployed condition leave a large surface area of material within the patient's body, wherein this large area of material may lead to the formation of thrombosis or cause a reaction in the patient's body.

Additionally, many devices on the market are configured such that the patients anatomy must be adjusted to fit the geometry of the device. For example, if the PFO consists of a puncture or small opening, a sizing balloon is passed through the opening to conform the opening to the size of the device, many times this involved tearing of the tissue to form a larger opening to receive the device.

Therefore there is a need for improved devices that can be easily deployed within a patient's anatomy without having to alter the patient's anatomy and while leaving the smallest amount of foreign material exposed to the patient's blood stream.

There is also a need for improved devices which when in a deployed state are physically anchored to the patient's anatomy thereby preventing the device from possibly migrating within the patient's anatomy over time and causing other complications.

These and other objects, advantages, and features of the invention will become apparent to those persons skilled in the art upon reading the details of the methods and systems of the present invention that are more fully described below.

SUMMARY OF THE INVENTION

In accordance with the present invention there is provided devices and methods for suturing intracardiac defects. The devices according to the present invention include a handle portion, an elongate shaft, and a foot housing having a deployable foot and at least two needles and a length of suture. According to the methods of the present invention the device is introduced to a patient's vasculature, wherein the foot housing of the device is passed through an intracardiac defect such as a patent foramen ovale, the foot is deployed and the device is pulled back against the septum primum and secundum. After placing the foot against the primum and secundum, at least one needle and more preferably two needles are deployed from the elongated shaft and received by the foot, thereby placing a suture loop between the primum and secundum. The suture loop may be terminated by tying a knot or using a suture-locking device, thereby closing the intracardiac defect.

In accordance with the present invention there is provided a suturing device having a housing having a foot actuation handle and a needle actuation handle, the housing having a proximal end and a distal end; a flexible shaft extending from the distal end of the housing, the flexible shaft having proximal end and a distal end; a foot housing extending from the distal end of the shaft, the guide carrying a pivotable foot, the foot being operative connected to a foot actuation wire, the foot actuation wire being connected to the foot actuation handle; at least one needle extending from the needle actuation handle and through the shaft; a length of suture having two ends, the length of suture positioned on the device; and a distal sheath extending from the foot housing, the distal sheath defining a guidewire lumen.

In accordance with the present invention there is provided a suturing device comprising: a housing; a elongate tubular member having a proximal portion and a distal portion; an elongate foot movably mounted within a foot housing; a foot actuation handle operatively coupled to the elongate foot, wherein movement of the foot actuation handle causes the foot to pivot from a low profile configuration substantially aligned with the foot housing to a deployed configuration extending at an angle from the foot housing; a pair of needles advanceable from the proximal portion of the shaft to the deployed foot, at least one needle having a distal end carrying a detachable tip, the detachable tip connected to a first end of a length of suture, the suture having a second end and a bight between the first and second ends, the bight being prearranged on the outer surface of the device to define a pre-tied knot or a suture loop, wherein the first end passes through the bight.

In accordance with the present invention there is provided a suturing device, comprising: an elongate housing having a proximal end and a distal end; a first foot mounted to move relative to said elongate body, said first foot including a needle receiving portion and being actuatable between a first and second position, said needle receiving portion being substantially within said housing in said first position and said needle receiving portion disposed outwardly away from said housing in said second position; a first needle having a distal end, said needle mounted to move longitudinally along at least a portion of the extension of said elongate body in a proximal to distal direction and into said needle receiving portion when said arm is in said second position; and a length of suture having a first end and a second end, at least one of the ends including a toggle disposed thereon.

In accordance with the present invention there is provided a method for suturing a patent foramen ovale, the method including the following steps: (a) providing a suturing device including a housing having a foot actuation handle and a needle actuation handle, a flexible shaft extending from the distal end of the housing, a foot housing extending from the distal end of the shaft, the guide carrying a pivotable foot, the foot being operative connected to a foot actuation wire, the foot actuation wire being connected to the foot actuation handle; at least one needle extending from the needle actuation handle and through the shaft; a length of suture, and a distal sheath extending from the guide, the distal sheath defining a guidewire lumen. (b) Advancing the suturing device through the inferior vena cava, right atrium, and patent foramen ovale such that the foot is positioned in the left atrium. (c) Deploying the foot to a deployed position; advancing the at least one needle through tissue and further into a needle receptacle, and (d) advancing at least one end of the length of suture through the tissue to suture the PFO.

DETAILED DESCRIPTION OF THE DRAWINGS

Preferred embodiment(s) of the present invention are described herein with reference to the drawings wherein like numerals have been utilized to denote similar components.

FIG. 1. is a plan view of a suturing device in accordance with the present invention.

FIG. 2a. is a cross-sectional view of the shaft of the suturing device taken about line 2-2 of FIG. 1.

FIG. 2b. is a plan view of an exemplary embodiment of a reinforcement layer in accordance with the present invention.

FIG. 3. is a cross-sectional view of the shaft of the suturing device of the present invention taken about line 3-3 of FIG. 1.

Figure 4:
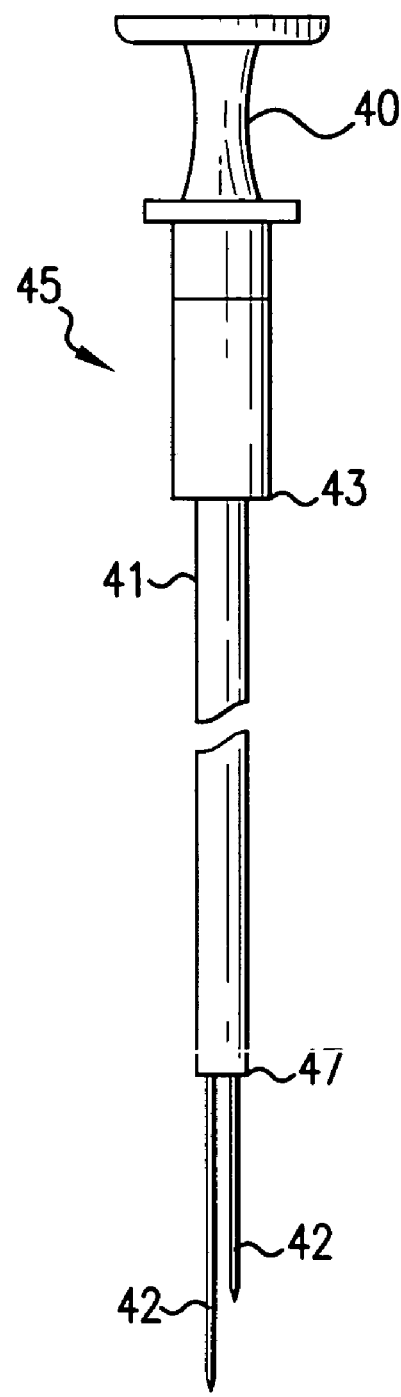

FIG. 4. is a plan view of the needle actuation assembly in accordance with the suturing device of the present invention.

Figure 5:
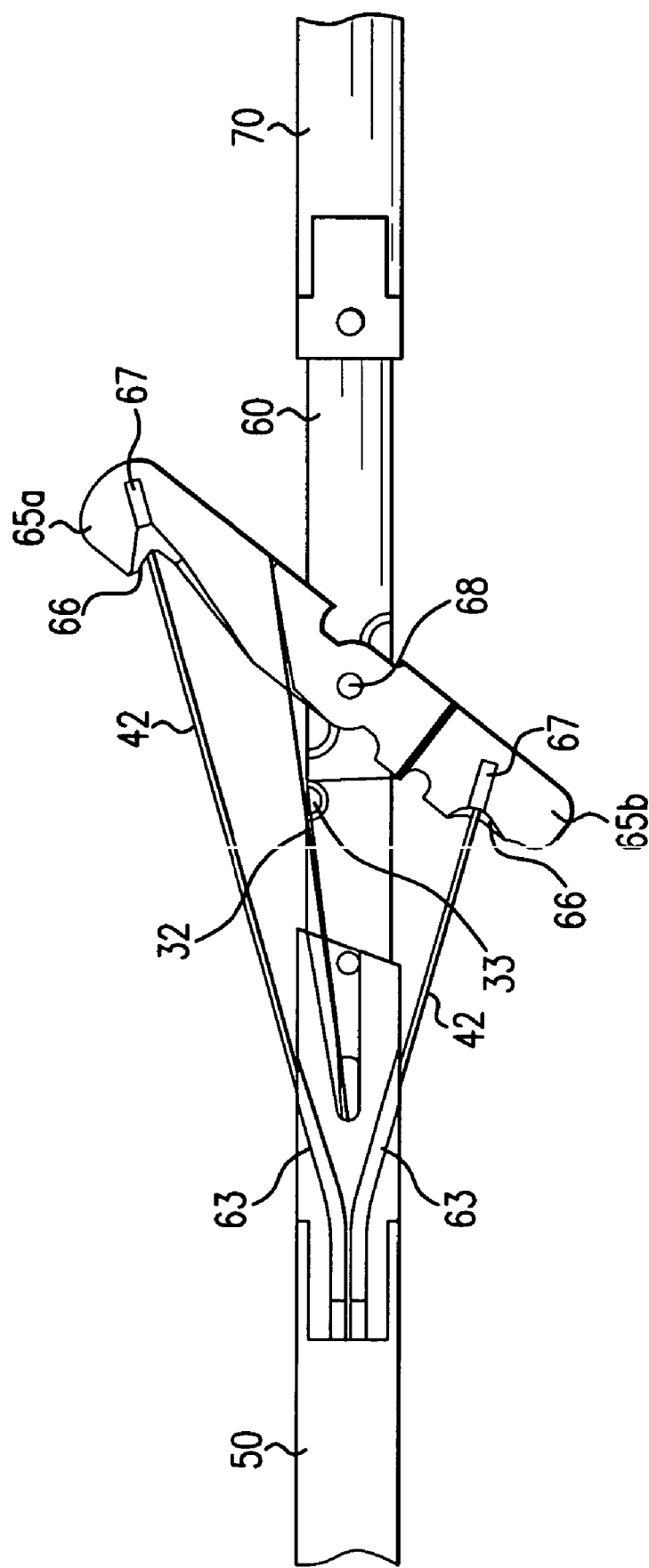

FIG. 5. is a cross-sectional view of the articulating foot of the suturing device in accordance with the present invention.

FIG. 6a. is a plan view of one embodiment of a suture that may be utilized in accordance with the device and methods according to the present invention.

FIG. 6b. is a plan view of an alternative embodiment of a suture and suture-locking device that may be utilized in accordance with the device and methods according to the present invention.

FIG. 6*c*. is a plan view of an exemplary embodiment of a sealing member in accordance with the present invention.

FIG. 6*d*. is a plan view of an alternative embodiment of a sealing member in accordance with the present invention.

Figure 7:
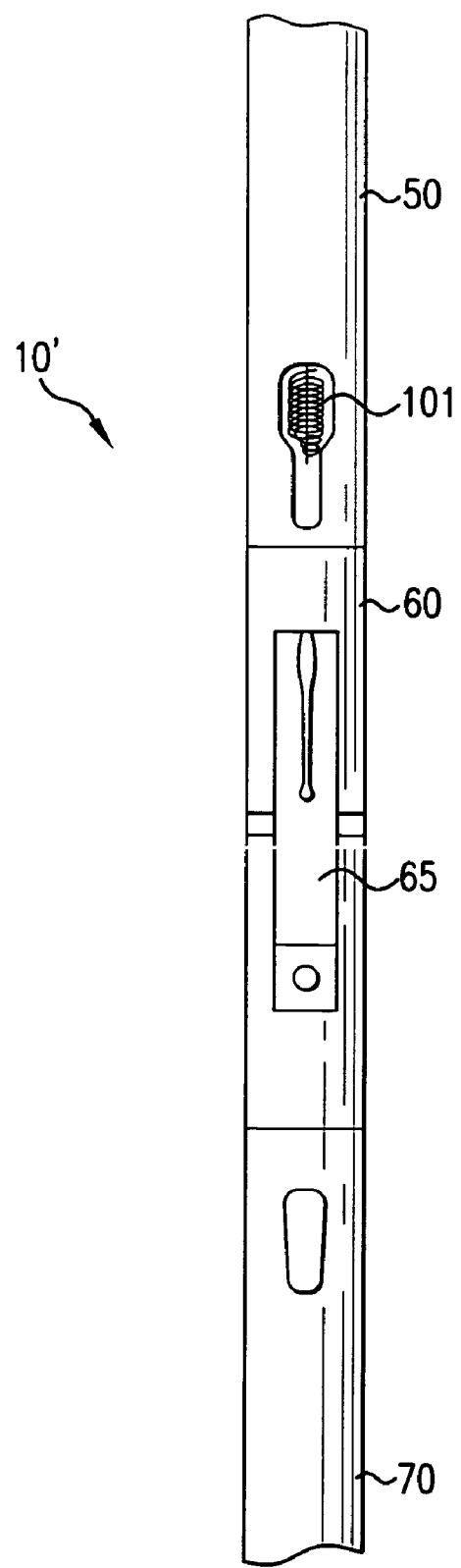

FIG. 7. is a partial view of an alternative embodiment of the device according to the present invention illustrating a pre-formed suture bight disposed about a needle and adjacent the foot of the device.

Figure 8:
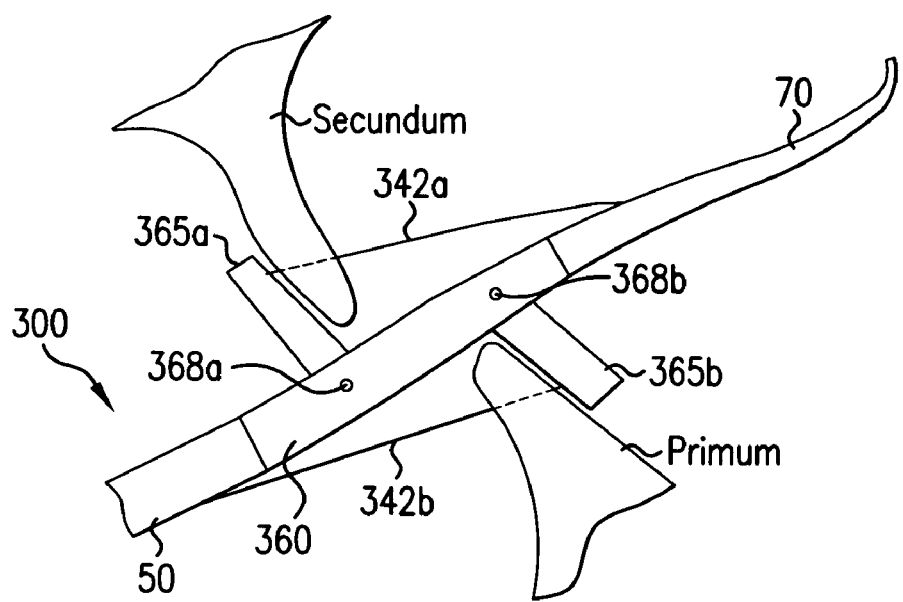

FIG. 8. is a partial plan view of an alternative embodiment of the foot and foot housing of the suturing device in accordance with the present invention.

Figure 9:
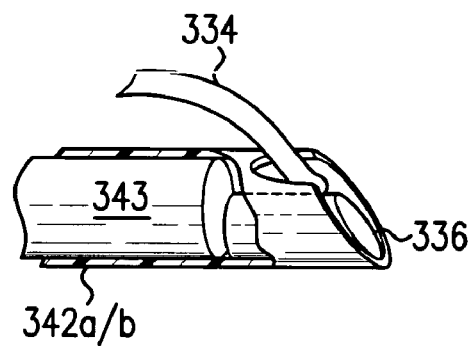

FIG. 9. is a cross-sectional view of a distal tip of an alternative embodiment of a needle and suture assembly according to the present invention.

Figure 10:
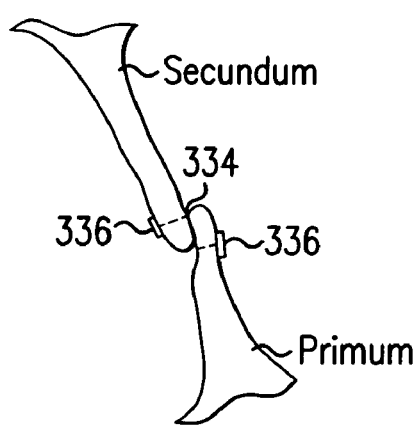

FIG. 10. is an exemplary embodiment of a suture path formed with the device according to FIGS. 8 and 9.

Figure 11:
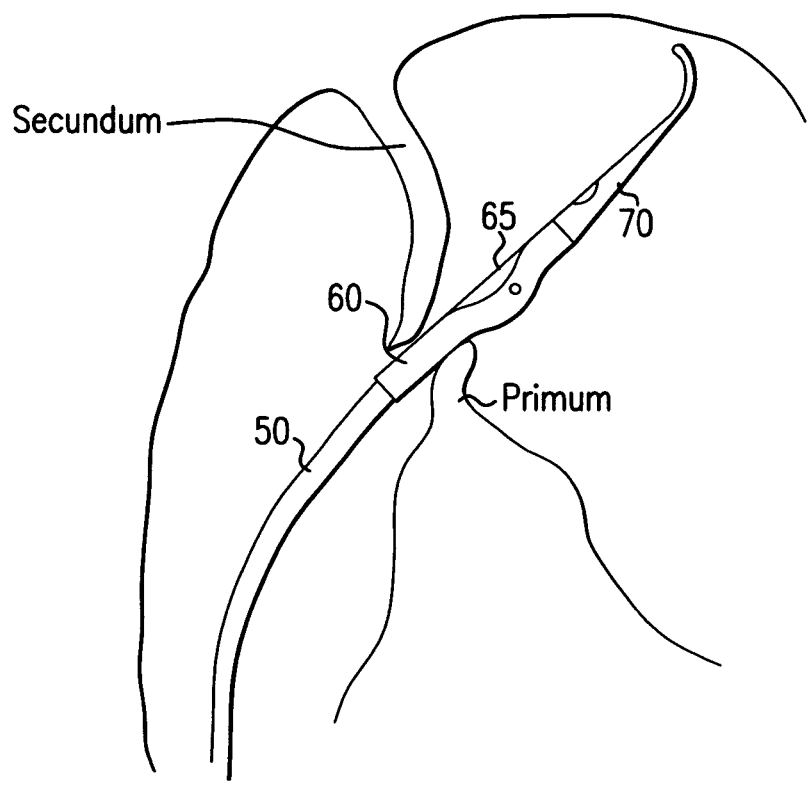

FIG. 11. is a plan view of a heart illustrating a PFO wherein the suturing device in accordance with the present invention is shown disposed through the PFO.

Figure 12:
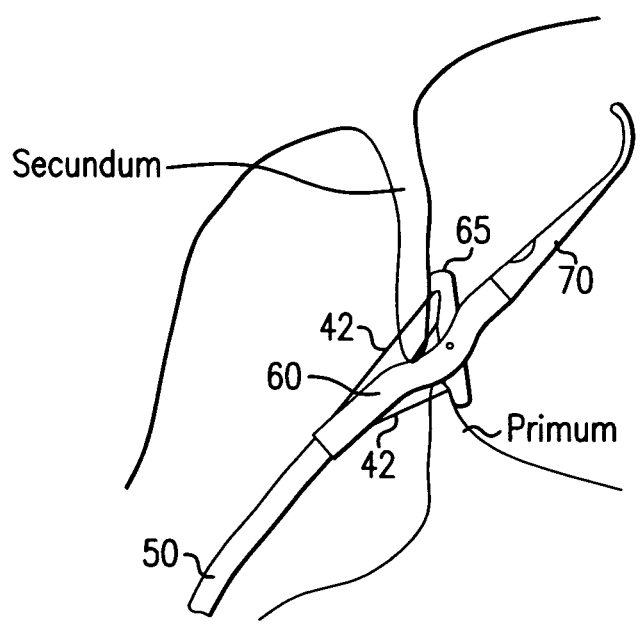

FIG. 12. is a plan view of a heart illustrating a PFO wherein the suturing device in accordance with the present invention is shown disposed through the PFO, wherein the articulating foot is shown in a deployed position.

DETAILED DESCRIPTION OF THE PREFERRED EMBODIMENTS

In accordance with the present invention there is provided a device and methods for closing intracardiac defects. The device according to the present invention include a handle portion, a flexible elongated member extending from the handle portion at one end and connected to a foot housing at the other end, a deployable foot disposed within the foot housing and a flexible distal tip. At least one needle and more preferably two needles are disposed within the flexible elongated member. The suturing device is configured to dispose a length of suture across the site of a PFO, wherein the suture is placed through the tissue adjacent the opening to close the opening. As described in more detail below, the suture is advanced through the tissue by a pair of needles that penetrate the tissue adjacent the opening, connect with the ends of the suture, and move the suture through the penetrations in the tissue to span the opening. A knot is then loosely tied with the length of suture and advanced to the site of the PFO. The tails of the suture extending from the knot are then cut and removed. It is further contemplated that a bight of suture may be pre-arranged on the body of the device, wherein after the suture has been passed through the tissue and across the opening, the bight of suture is detached and forms a knot or a suture loop, wherein the knot or suture loop may be advanced to close the opening. Still further it is contemplated that a suture-locking device may be utilized in the place of a knot to effect a closure of the opening. Examples of a suitable suture-locking device can be seen in U.S. provisional patent application having Ser. No. 60/502,295 filed Mar. 15, 2004 and U.S. the entirety of which is hereby incorporated by reference.

In accordance with alternative embodiments of the device in accordance with the present invention, the device may be utilized to dispose other types of closure devices across the PFO. For example, in accordance with one alternative embodiment, a suture having a self-tightening feature may be disposed across the opening, wherein after being placed across the opening the opening may be closed by applying a force to one end of the suture. In another alternative embodiment, the suture ends may have a pre-scored line or feature that is configured to sever the suture above a knot in response to a pre-determined force being applied to the end of the suture. These and other alternative embodiments will be described in greater detail below with reference to the appropriate drawing figure.

The suturing device according to the present invention preferably includes a housing at its proximal end that functions as the main handle or control portion of the device. The housing has associated with it a movable or pivotable foot handle and a movable or slidable needle actuation handle. A flexible shaft extends from the distal end of the housing. A foot housing is attached to the distal end of the flexible shaft. The foot housing carries a pivotable foot. A distal sheath is attached to the distal end of the foot housing, wherein the flexible shaft further includes at least one suture and one needle disposed therein and more preferably at least two needles. The foot further includes a flexible filament, one end being configured to receive a first needle tip and the second configured to be received by the second needle as will be described in greater detail below with reference to the appended figures.

As shown in FIG. 1, the suturing device 10 includes a handle assembly including a handle portion 20 having proximal and distal ends. A foot actuation lever 30 being pivotally associated with the handle portion 20 and disposed adjacent the proximal end of the handle portion 20. A flexible shaft 50 extends from the distal end of the handle portion 20, wherein the distal end of the flexible member 50 being associated with a foot housing 60. The foot housing having a proximal end and a distal end, the proximal end being coupled to the distal end of the handle portion 20 through flexible shaft 50 and the distal end of the foot housing coupled to the distal sheath 70. The suturing device 10 further including a needle actuation handle 40, wherein the needle actuation handle extends from the proximal end of the handle portion 20, wherein the needle actuation handle 40 is operationally coupled to at least one needle and preferably two needles disposed within the handle portion 20 and the flexible shaft 50 as will be described in greater detail below. The foot actuation lever 30 is operatively coupled with a foot 65, wherein the toot 65 is disposed in a foot housing 60.

As shown in FIG. 1, the distal sheath 70 is preferably constructed of a flexible material such as Pebax. The sheath is a generally tubular member that defines a guidewire lumen communicating with and extending between a guidewire entry port 72 and a guidewire exit port 73. The length of the distal sheath may be about 1 inch to about 6 inches and more preferably between about 2 and about 4 inches. The distance between the guidewire entry and exit ports may be between about 1 inch to about 6 inches and preferably between about 2 and about 4. The distal sheath may be tapered in the distal direction and may have a J-tip or a straight tip at its distal end. The flexibility of the distal sheath, in one embodiment, progressively increases in the distal direction. It is contemplated that the length of the distal sheath my be chosen such that the distal sheath has sufficient length to be received within the pulmonary vein to further align the device within a patient's anatomy.

As shown in FIG. 1, the proximal end of the flexible shaft 70 is coupled to the distal end of the foot housing 60. The foot housing 60 is configured to house a foot 65, wherein the foot 65 is configured to be pivotally attached to the foot housing 60. Foot 65 is configured to move between a low profile delivery configuration, in which the foot is substantially housed and aligned along an axis of the foot housing 60 (as illustrated in FIG. 1), to a deployed position, in which the foot extends laterally from the shaft, upon actuation of foot actuation handle 30 disposed on proximal housing 20 as shown in FIG. 5.

In the delivery configuration illustrated in FIG. 1, the foot 65 extends substantially along and within the foot housing 60. As shown the foot housing 60 may have a curved portion, the curved portion being particularly adjacent the foot 65 wherein the apex of the curve of the foot housing 60 may be centered about the pivot point 61 of the articulating foot 65. In the exemplary embodiment, foot 65 is substantially disposed within a foot housing 60 so as to minimize the cross-section of the device adjacent the foot prior to deployment. Advantageously, prior to deployment of the foot 65, device 10 can have a cross-section adjacent foot 65 between about 6 and 18 Fr and more preferably between about 8 and 12 Fr.

As described above, the foot housing 60 preferably includes a curved portion disposed between the proximal and distal end of the foot housing, wherein the curved portion of the foot housing 60 is configured to aid in placement of the device 10 within the patient's anatomy as well as enhance tissue capture as will be described in greater detail below with regard to the methods in accordance with the present invention.

The proximal end of the foot housing 60 is coupled to a flexible shaft 50, wherein the flexible shaft 50 is an elongate tubular shaft constructed having a degree of flexibility sufficient to allow the flexible shaft 50 to be advanced through tortuous blood vessels, arteries and/or body cavities. The flexible shaft 50 preferably has adequate column strength to resist buckling during deployment of the foot 65, i.e., when tension is applied to a deployment wire 32 extending through the lumen of the shaft between the foot deployment handle 30 at the proximal end of the flexible shaft 50 and the foot 65 at the distal end of the flexible shaft 50. The inner and outer surfaces of the shaft may be covered with a polymer sleeve or coating such as Pebax. The flexible shaft 50 may have a length between about 10 inches and about 48 inches, more preferably between about 18 and about 36 inches.

Referring now to FIG. 2a, there is shown a cross-sectional view of the flexible shaft 50 taken about line 2-2 of FIG. 1. As shown in FIG. 2a, the flexible shaft 50 may be formed of multiple layers, each layer having different mechanical properties. For example, the flexible shaft 50 may be constructed having inner layer 51 and outer layer 52 formed of flexible materials such as polyurethane or polyvinylchloride (PVC) wherein a middle reinforcing layer 53 is sandwiched between the two layers. The reinforcing layer 53 is preferably disposed between the inner layer 51 and the outer layer 52. In one embodiment, the reinforcing layer 53 includes braided material. For example, the reinforcing layer 53 can be provided in the form of a braided stainless steel tube or sheet. Preferably, the braid includes flattened filaments, as opposed to having filaments with a round cross-section. Although a metallic braided is preferred, it is not necessary. It is also possible to provide a woven fabric or appropriately oriented filaments, such as carbon fibers encased in a polymeric matrix. Likewise, such reinforcing fibers could additionally or alternatively be incorporated into the inner layer 51 and/or the outer layer 52 during the manufacturing process. The reinforcing layer 53 need not be present through the entire length of the flexible shaft 50. For example, it is possible for reinforcing layer 53 to be provided along the proximal portion of shaft 50 only, or some greater or lesser portion.

Suitable materials of which the inner and outer layers of the flexible shaft 50 may be constructed from include polymeric materials such as PEEK and preferably traverses substantially the entire length of the flexible shaft 50. However, any of a variety of materials can be used for the inner and outer layers of the flexible shaft 50. For example, flexible shaft 50 could be made from other polymers such as PTFE, PVDF, Kynar, or polyethylene of various suitable densities.

In an alternative embodiment, one or more than one layer of the flexible shaft 50 may be constructed from a metallic material such as Nitinol or stainless steel, wherein reliefs may be formed in the wall of the metallic material to provide flexibility. As a further alternative, the flexible shaft 50 can be a composite member comprising a fabrication of several different materials, such as a co-extrusion of different polymers, or fiber-reinforced composite material such as fiber-reinforced resin material.

Additionally as shown in FIG. 2a, the flexible shaft 50 further includes at least one foot actuation wire and more preferably two foot actuation wires 32, two needles 42, and a suture storage lumen 80. The suture storage lumen may be a separate elongated tube disposed within the flexible shaft 50, or the flexible shaft 50 may be constructed having multiple lumens integrally formed therein, where one lumen would be configured as a suture storage lumen 80, another lumen may be configured to contain one or more of the needles or actuation wires 32.

Referring now to FIG. 2b, there is shown a plan view an exemplary embodiment the metallic reinforcing layer 53 of the flexible shaft 50. For purposes of illustration and not limitation, as embodied herein, tubular wall of the metallic member preferably has one or more perforations 54 defined therein. The perforations 54 generally are oriented circumferentially about tubular wall of the metallic member. Preferably, in accordance with this exemplary embodiment of the invention, the perforations 54 are disposed circumferentially about wall in pairs so as to define hinge points 55 therebetween. As depicted, each perforation 54 subtends an angle of less than 180 degrees of the circumference of cylindrical wall. However, a single perforation subtending an angle greater than 180 degrees is also within the scope of the invention. Perforations 54 can be formed by laser discharge, milling, etching or any other suitable techniques. Collectively, perforations 54 are preferably sized and shaped, and spaced from one another to modify the flexural characteristics of the flexible member 50 in a predetermined manner without altering the compressibility of the flexible shaft 50. For example, alternating pairs of perforations 54 can be rotated with respect to each other by a predetermined angle, such as 90 degrees. In this manner, it is possible to provide for enhanced flexure of the flexible shaft 50 in two directions that are substantially perpendicular to one another. Similarly, the longitudinal spacing between perforations can be varied to provide for varying rigidity along the length of the flexible shaft 50. Likewise, the circumferential placement of perforations 54 can be varied to impart desired bending characteristics to the flexible shaft 50. Additional spacings between perforations along the length of the flexible shaft 50 may be implemented, if desired, to vary flexural characteristics gradually, or in a step like fashion.

There are many ways in which the perforations 54 can be shaped and arranged in accordance with the invention. In one embodiment, the perforations can be varied in size and/or in longitudinal spacing to create regions of greater or lesser axial flexibility. Furthermore, alternating pairs of perforations 54 need not be alternated merely by rotating them 90 degrees. Any pattern of rotation to create a desired bending characteristic can be achieved. Moreover, the perforations do not need to be circumferentially aligned slit shapes. For example, and in accordance with an alternate embodiment of the invention the perforations 54 may include longitudinal components, such as an I-shape. In accordance with this aspect of the invention, perforations 54 include a circumferential component and a longitudinal component. A variety of other shapes and arrangements are possible for perforations 54. For example, the perforations can be ellipsoidal in shape or could take the form of a curved slot or be formed such that the perforations 54 form articulating joints having male and female components that are pivotally coupled.

In yet another alternative embodiment, the flexible shaft 50 may be formed of one or more coil assemblies. It is contemplated that two coil assemblies can be utilized to form the flexible shaft 50 or at least one layer of a multiple layer flexible shaft as described above. Wherein an inner coil would be wound having a specific pitch and the outer coil would be wound having a specific pitch, wherein the coils' pitches define flexible properties of the flexible shaft 50. The flexibility of the flexible shaft 50 may be further tuned or adjusted by varying the thickness of the material from which the coil assemblies are constructed of.

The flexible shaft 50 may further include a pre-formed curve disposed adjacent to the proximal end of the foot housing 60 as shown in FIG. 11.

The pre-formed curve in the flexible shaft 50 aligns the foot housing 60 nearly perpendicular to the PFO within the septum as shown in FIGS. 6 and 7 and will be described in greater detail below with regard to the methods according to the present invention. By aligning the device nearly perpendicular to the PFO, tissue capture on the superior side of the PFO is greatly enhanced since the needle is nearly perpendicular or perpendicular to the superior side of the PFO. The angle of the pre-formed curved section is formed so that the device fits within the anatomy of the right atrium and across the PFO naturally. It shall be understood that the angle of the device may be adjusted prior to insertion of the device by bending, heat forming or similar methods. It is further contemplated that a steering device or mechanism may be integrated into the flexible shaft 50, wherein an adjusting member coupled to the steering device disposed on the handle portion 20 may be utilized to adjust the angle of the pre-formed curved portion of the flexible shaft. The pre-formed curve section may have an angle between about 0 and 180 degrees, more preferably between about 10 and 80 degrees and most preferably between about 30 and 60 degrees. It is further contemplated that an introducer sheath/catheter may be utilized to position the device 10 in accordance with present invention, wherein the introducer would have a pre-formed curve disposed therein and be utilized to locate the device 10 within the PFO as described above.

Referring now to FIG. 3 there is shown a cross-sectional view of the flexible shaft 50 taken along line 3-3 of FIG. 1. The cross-section shown in FIG. 3 is at a location along the length of the shaft proximal to the cross-section of FIG. 2. At the location shown in FIG. 3, the needle actuation shaft 41 is shown, as well as the suture storage lumen 80 and the foot actuation wires 32, each of which will be described in greater detail below.

Referring now to FIG. 4, there is shown the needle assembly 45, wherein the needle assembly includes a needle actuation handle 40, a needle actuation shaft 41 and at least one needle 42, and more preferably at least two needles 42. As shown in FIG. 4, the needle actuation shaft 41 is a generally elongated member having proximal 43 and distal 47 ends, wherein the proximal end 43 is coupled to the distal end of the needle actuation handle and the distal end 47 is configured to fixedly receive the proximal end of the needles 42. The two needles 42 may be force fit into the distal end 47 of the needle actuation shaft 41. Alternatively, a needle-retaining feature, such as a proximally extending barb, may be provided on the proximal end of the needle 42, wherein the distal end 47 of the needle actuation shaft may be overmolded, thereby capturing the needles in a fixed position. Still further, it is contemplated that the needles may be attached to the needle actuation shaft utilizing other attachment methods such as glues, welding, friction/interference fit, or through the use of locking features.

The needle actuation shaft 41 is preferably constructed having good flexibility while exhibiting good compressive strength. The needle actuation shaft 41 may be constructed in a similar manner to the flexible shaft 50, wherein the needle actuation shaft may be constructed of multiple layers or as a composite member. For example, the needle actuation shaft may include a metallic core such as that shown in FIG. 2b, wherein the metallic core is covered with a plastic covering. Alternatively, the needle actuation shaft may be formed from a unitary member such as a plastic or metallic tube or rod. Suitable metallic materials include stainless steel, nitinol, high tensile stainless steel or similar metals.

In a preferred embodiment and as shown in FIG. 4, one needle 42 preferably has a length greater than the other needle. The difference in lengths of the needles is so that the tips of the needles will engage the respective needle receptacles 66 in the foot 65, when the foot 65 is pivoted to a deployed position that is at a non-perpendicular angle to the axis of the foot housing 65 as shown in FIG. 12. It is further contemplated that at least one of the needles may be constructed having a detachable needle tip 49, wherein the detachable needle tip is configured to disengage from the shaft of the needle 42 when the detachable needle tip 49 is received within the needle receptacle 66 of the foot 65 as will be described in greater detail below with regard to the methods according to the present invention. Additionally, one end of the suture 34 is configured to be attached to the detachable needle tip 49, therefore, when the detachable needle tip 49 is detached from the needle 42, the suture 34 remains with the detached needle tip 49.

Referring now to FIG. 5, there is shown an enlarged view of a portion of the foot housing 60, wherein the foot 65 is illustrated in a deployed configuration. In order to advance the foot from the delivery configuration to a deployed configuration, the foot actuation handle 30 pivotally disposed on the handle portion 20 is moved from a first position generally flush with the handle portion to a second position disposed at an angle to the handle portion 20. The actuation of foot handle 30 slides one of the foot actuation wires 32 proximally, pulling foot 65 from a parked position shown in FIG. 1, to the deployed position illustrated in FIG. 5. Once deployed, a first end 65a and a second end 65b of foot 65 extend laterally from the foot housing 60 at an angle relative to the foot housing. The distance between the first end 65a of the foot and the foot housing 60 is greater than the distance between the second end 65b of the foot and the foot housing 60, wherein the pivot point of the foot 65 is not disposed about a symmetrical axis of the foot 65. The first end 65a of the foot is longer than the second side 65b of the foot to help prevent the foot from being pulled back through the atrial septum during the procedure. An exemplary ratio of relative lengths of the two sides of the foot may be 1.5 to 1.0.

To return the foot 65 to the delivery configuration from the deployed configuration, the foot actuation handle 30 is pivoted towards the first position, which causes the foot actuation wire 32 connected to the second side of the foot 65 to be pulled in the proximal direction to pivot the foot 65 back to the delivery configuration, wherein the foot 65 is substantially aligned with the foot housing 60. As shown in FIG. 5, a bearing 33 is positioned proximal to the pivot point 68 of the foot 65 to provide a surface against which the foot actuation wires 32 slide. The bearing 33 is positioned such that the foot actuation wires 32 are routed over the bearings 33 to change the direction of the pulling force against the foot 65. In particular, the wire 32 attached to the inferior side 65b of the foot 65 is routed so that the pull force is transmitted to the foot at an angle that is roughly perpendicular to the lever arm of the foot 65 with respect to the pivot point 68 of the foot. This is to insure that the foot 65 may be fully returned to the delivery configuration wherein the foot 65 is substantially aligned with the foot housing 60.

The pre-formed curve in the foot housing 60 of the device 10 as shown in FIG. 1 enables the device 10 to fit within the patient's anatomy by disturbing the PFO superior septum flap less due to the pre-formed curve portion while at the same time increasing tissue capture by favoring capture on the superior side, and minimizing needle free flight length. The pre-formed curve sections may be manufactured according to the intended use of the device 10. For example, a different curve may be required if the device is to be used in the right atria vs. a device that is intended to be utilized in the left atria. Further still, the device may be manufactured wherein multiple foot housing geometries may be provided, such that during a procedure a surgeon may choose an appropriate foot housing geometry based upon the patient's anatomy.

The foot 65 further includes needle receptacles 66 adjacent the ends 65a and 65b of the foot, wherein the receptacles are configured to retain a cuff 67. The two cuffs 67 are coupled together with a flexible filament (not shown), wherein the flexible filament is configured to be disposed along the length of the foot. The flexible filament may comprise a length of suture, a length of wire, Teflon, nitinol, or similar materials. Additionally, the cuffs are configured to receive the ends of the needles 42. The suture 34 in accordance with the present invention may comprise a continuous filament with one end attached to the detachable needle tip and the other end attached to the other needle.

In the deployed position, the angle of the foot relative to the guide portion is approximately less than 90 degrees, more preferably less than 80 degrees and most preferably about 51 degrees. The deployed angle may be selected to be any angle that provides optimal apposition of the foot against the tissue surface that is to be sutured, because the atrial septum, including the septum primum and the septum secundum, will vary in physical orientation, size and thickness from patient to patient.

The foot housing 60 in accordance with the present invention may be constructed of stainless steel for enhanced visualization under fluoroscope. Alternatively, the foot housing may be constructed of a non-radiopaque material wherein radiopaque markers may be provided on the foot housing 60 or the foot 65 to further enhance radiopacity of the device during the suturing procedure. As descried above, in addition to retaining the pivotable foot 65, the foot housing may further include needle guide paths (not shown) that direct the needles 42 away from the axis of the foot housing 65 and toward the needle receptacles 66 and the cuffs 67 disposed within the foot 65. Alternatively, radiopaque markers may be disposed along the length of the flexible shaft 50 or along the length of the distal sheath 70.

In another embodiment (not shown), the foot 65 may include multiple pairs of needle receptacles 66. Such an embodiment may be desirable when more than one suture loop will be used to suture the PFO. The needle receptacles 66 may be oriented in a side-by-side fashion with respect to the length of the foot 65, or in a longitudinal orientation on the foot. As such, additional pairs of needles 42 and suture 34 will also be provided in addition to the multiple needle receptacles 66.

The various embodiments of the suturing device 10 in accordance with the present invention may include any of a variety of types of suture, such as braided or monofilament. The suture material may be absorbable or nonabsorbable and may be made of polyester, polypropylene, polyglycolic acid, nylon, silk or any of a variety of suture materials known in the art. Suture material coated with antibiotics or other antimicrobial agents may also be provided with the suturing devices of the present invention.

An exemplary suture material is TEVDEK II®, a braided polyester suture material that is impregnated with PTFE and manufactured by Genzyme Biosurgery of Cambridge, Mass. An exemplary monofilament suture material is DEKLENE II®, a polypropylene suture material also manufactured by Genzyme Biosurgery. Another exemplary monofilament suture material is nylon monofilament, also manufactured by Genzyme Biosurgery.

Monofilament suture material tends to be stiffer relative to braided suture material. As such, forming a bight of suture for the purpose of providing a pre-tied knot is more difficult with monofilament suture than with the more flexible braided suture. The monofilament suture material will tend to straighten itself out after being looped to form a bight as previously described. Therefore, in order to provide a bight of monofilament suture that is releasably disposed on the shaft of the device without unraveling the loops forming the bight are heated to set the bight. The heating of the bight of monofilament suture to set the bight is performed after the suture has undergone any manufacturing procedures that may include drawing, annealing or any other procedure that employs heat to manufacture the suture material.

Further still, the device 10 in accordance with the present invention may be utilized with modified suture, wherein the suture may be modified to provide retention in tissue. One example of such a suture can be seen with regard to FIG. 6a, as shown in FIG. 6a, the suture 134 includes a first end 133 and a second end 135, wherein a knot 136 is formed in the suture adjacent the second end 135. In use, the suture is delivered across an opening, wherein the first end of the suture 133 is utilized to tighten the suture 134 and close the opening. By applying a force to the first end 133 of the suture, the knot 136 is advanced along the length of the suture. A feature 137 disposed at the second end of the suture 135 prevents the second end of the suture 134 from being drawn through the knot 136, wherein the applied force causes the knot 136 to tighten. The knot 136 may be formed such as a clinch knot, sliding knot, bowline, half-hitch or similar knot styles.

Referring now to FIG. 6b, there is shown an alternative embodiment of a suture that may be utilized with the device 10 in accordance with the present invention. As shown in FIG. 6a, the suture 234 may have a locking element 236 disposed on a second end 235 of the suture, wherein a plurality of beads 237 are formed along the length of the suture 234 as shown in FIG. 6b. In use, the suture 234 is disposed across an opening, wherein the first end 233 of the suture is passed through the locking element 236 disposed on the second end 235 of the suture 234. The beads 237 formed along the length of the suture pass through the locking element 236, wherein the locking element 236 is designed to only allow the beads 237 to pass through in one direction, thereby effectively closing the opening. The beads 237 may be heat formed, mechanically formed, or integrally formed along the length of the suture 234 or may be formed as knots. It is further contemplated that locking element 236 may be embodied in the form of a knot similar to those described above with regard to FIG. 6a.

It shall be understood that the sutures described above and shown herein are examples of suitable sutures that may be utilized with the device and methods of the present invention and should not be considered limiting in any manner. Further still, the ends of the suture may be distinguished from each other by changing the color of one end (e.g. with dye), providing an attachment on one end (e.g. shrink wrap tubing, a bead, etc.) or with the suture itself (e.g. tying a knot in one end). Alternatively, one end of the suture may be colored through a dye process.

It is further contemplated that a sealing member may be utilized in combination with the device and methods according to the present invention.

Examples of exemplary sealing members can be seen with reference to FIGS. 6c and 6d, where there is shown two sealing members which may be utilized with the methods according to the present invention as will be described in greater detail below.

Referring now to FIGS. 6c and 6d there is shown an exemplary embodiment sealing members which may be additionally be included for use with the devices and methods in accordance with the present invention. Referring now to FIG. 6c, there is shown a sealing member 250 includes a first end 253 and a second end 255 wherein the first end includes at least one suture aperture 252 and more preferably at least two suture apertures. The suture apertures may be constructed having a locking feature, wherein the suture is passed through the suture apertures 252, wherein as the sealing member 250 can then be only advanced in one direction along the length of the suture, thereby tensioning and locking the suture disposed across the opening. The sealing member 250 may be constructed of a biocompatible mesh material such as PTFE, Nylon, nitinol or similar materials, wherein the sealing member is configured to be disposed on between the patient's tissue forming the PFO and the knot or suture clip device. The sealing member may be configured to be an expandable member, or other types of sealing devices. For example, the sealing member may further include a gel, foam, glue, or similar sealing products, or the sealing member may be constructed of a bioabsorbable material such that the sealing member would be eventually absorbed. Further still, the sealing member may be integrally formed with the suture clip device, wherein both the sealing member and the suture clip device can be deployed in a single action.

Refeffing now to FIG. 6d there is shown a cross-sectional view of an alternative embodiment of a sealing member 260 in accordance with the present invention. As shown in FIG. 6d, the sealing member 260 includes a base member 261 and a locking member 263, wherein the base member and the locking member are preferably constructed of biocompatible materials. The base member may be constructed in a manner such that the base member has a first diameter and a second diameter, wherein the first diameter may be a delivery diameter and the second diameter is greater than the first diameter. For example, the base member may be constructed having a metal support structure formed of nitinol and a membrane covering, wherein the nitinol metal frame expands upon delivery. The base member further includes at least one lumen formed therein, the lumen configured to receive at least one suture therethrough. The membrane covering the frame of the base member may further include a gel, foam, glue, or similar sealing products, or the base member may be constructed of a bioabsorbable material such that the base member would be eventually absorbed. The locking member 263 is configured to receive at least one suture and fixedly retain the suture in relation to the locking member.

Referring now to FIG. 7, there is shown a partial plan view of an alternative embodiment of the closure device 10 in accordance with the present invention. As shown in FIG. 7, the device 10' includes a suture bight 101 detachably attached to the device adjacent the foot housing 60. The bight of suture 101 is disposed within an opening formed in the tubular member 50, wherein the bight 101 is detachably attached to the flexible shaft 50. In use, the foot 65 is deployed, the loop of suture 34 serves to pull the bight of suture 101 down a rail portion of the suture during deployment. It should be noted that it would be desirable to be able to distinguish the ends of the suture 34 as described above, such that during deployment the correct end of the suture is pulled by the operator to advance the bight of suture 101 to form a knot. Should the non-rail end be pulled, the knot may be prematurely tightened before it is advance to its deployed position at the wall of the vessel.

Referring now to FIG. 8, there is shown an exemplary embodiment of a distal end of an alternative embodiment of a foot housing and foot member in accordance with the present invention, wherein like numbers have been used to denote components described above but not shown. As described above, the suturing device 300 shown in FIG. 8 includes a handle member 20 (not shown) including a foot actuation lever 30 (not shown) and a needle actuation handle 40 (not shown) and an elongated flexible shaft 50, a foot housing 360 and a distal sheath 370. As shown in FIG. 8, the device 300 includes a first foot 365a and a second foot 365b as well as first and second needles 342a and 342b. As shown in FIG. 8, the first foot 365a pivots about first pivot point 368a and the second foot 365b pivots about second pivot point 368b, wherein the first and second pivot points are offset from one another. Further still, the first and second foot 365a and 365b may be operated independently of one another or simultaneously. As shown the first foot 365a is configured to engage a proximal surface of the septum secundum and the second foot 365b is configured to engage a distal surface of the septum primum. After the foot members 365a and 365b have been deployed, the needles 342a and 324b are advanced, thereby penetrating the septum primum and septum secundum respectively. After the needles have been advanced through the tissue, the tips of the needles engage the foot members. As shown in FIG. 9 pusher member 343 disposed within a lumen of one of the or each of the needles 342a and 342b is activated to expel suture 334 having a toggle 336 attached to an end thereof from the lumen formed in the needle 342. After the suture(s) have been deployed, the needles and foot members can be retracted, wherein the suturing device 300 may then be retracted from the patient, thereby leaving a suture member 334 disposed across the PFO. The toggle 336 may be fixedly attached to one end of the suture and be slidably attached to the other end of the suture, wherein the slidable toggle 336 is configured to slide in only one direction in a similar manner to the suture locking system previously described. In use, the slidable toggle may be advanced along the length of the suture, wherein the toggle grasps and retains the suture. An exemplary embodiment of the suture path formed by the suturing device 300 can be seen with reference to FIG. 10.

Methods of Use

A procedure for closing a PFO using a suturing device in accordance with the principles of the invention is now described. Subcutaneous access to the right common femoral vein is gained via a puncture in the groin area of a patient. A trans-septal sheath or similar sheath with a dilator is advanced through the puncture, into the femoral vein and further through the inferior vena cava. The sheath may be further advanced into the right atrium of the heart. In one embodiment, the sheath defines a slight curvature at its distal end to match the anatomy of the patient. After placing the sheath in a desired location-the dilator is removed from the sheath, thereby leaving the sheath within the patient's vasculature.

A guidewire is advanced through the sheath and further into the right atrium. The guidewire is advanced through the PFO, through the left atrium, and may be further advanced into the pulmonary vein. The distal end portion of the guidewire can be positioned in the pulmonary vein to remain there for the duration of the procedure. Alternatively, the guidewire may be advanced through the PFO without the use of a sheath.

The suturing device in accordance with the present invention may then be advanced over the guidewire. The device is advanced into the heart such that the foot is positioned past the atrial septum as shown in FIG. 11. Proper placement of the device may be determined through the use of imaging technologies such as X-ray or fluoroscopy, wherein the radiopaque foot housing can be visualized relative to a patient's anatomy. Further still, it is contemplated that the device may include a pressure sensor disposed adjacent to the foot or foot housing, wherein a change in pressure or a pressure fluctuation may be used to determine location of the device within the patient's anatomy. In yet another embodiment, it is contemplated that the suture device in accordance with the present invention may include a bleedback port or other visible marking device, which may be used to determine placement of the device. After the device has been properly placed within the atrium of the patient and the foot housing is advanced a sufficient length into the patient's atrium, the foot 65 may be deployed from the foot housing 60 as shown in FIG. 10. To deploy the foot, the user applies a force to the lever 30, thereby applying a force to the actuation wires 32. Once the foot 65 is deployed, the suture device is pulled back slightly such that the foot contacts the atrial septum. By pulling slightly back on the device the atrial septum is pulled up against the foot 65 of the device 12, thereby increasing the likelihood of needle penetration and tissue capture. Additionally, by pulling back on the device the physician is provided with tactile feedback ensuring that the foot 65 has been properly deployed and engaged with the septum primum and secundum. The needle actuation handle 40 is then pressed to advance the needles 42 through the tissue and into the cuffs 67 disposed in the receptacles 66 formed in the foot 65.

In one embodiment, one of the needle tips carrying one end of the suture will detach from the needle shaft and be received by a needle cuff. The second needle will be received by a second needle cuff, wherein the needle and needle cuff will remain attached to one another, wherein each of the needle cuffs area interconnected to one another with a flexible filament or a short length of flexible material such as that described above. The needle actuation handle 40 is then pulled out of the housing of the device to remove the needles and pull the length of suture proximally, thereby positioning a loop of suture across the PFO.

The foot 65 is then advanced from the deployed configuration to a delivery configuration and the device may then be removed from the patient.

A knot may be tied, or advanced if the suturing device includes a bight or pre-formed knot which is deployed during the needle advancement step. It is further contemplated that a suture lock or clip may be used to secure the ends of the suture and close the opening in the atrium in place of forming a knot. Further still, a sealing member such as that shown in FIG. 6*c* and 6*d* may be disposed along the length of the suture prior to the formation of a knot or deployment of a suture-locking device. The tails of the suture may then be cut from the knot. In yet another alternative embodiment, the tails of the suture may be severed by applying a pre-determine amount of force to the tails of the suture, wherein the tails of the suture will sever due to the applied force. The severance of the suture tails in this embodiment may be further enhanced with the addition of a feature or features formed along the length of the suture thereby forming a weakened zone or region.

While the exemplary embodiments have been described in some detail for clarity of understanding, a wide variety of modifications, adaptations, and changes will be apparent to those of skill in the art. Hence, the scope of the present invention is limited solely by the appended claims.

The invention claimed is:

1. A method for suturing a patent foramen ovale (PFO), the method comprising:

providing a suturing device including a housing having a foot actuation handle and a needle actuation handle, the housing having a proximal end and a distal end; a flexible shaft extending from the distal end of the housing, the flexible shaft having a proximal end and a distal end; a foot housing extending from the distal end of the shaft, the foot housing defining a pre-formed curve portion formed to carry a pivotable first foot, the first foot being operatively connected to a foot actuation wire, a pivotable second foot, the second foot being operatively connected to the foot actuation wire the foot actuation wire being connected to the foot actuation handle; at least one needle extending from the needle actuation handle and through the shaft; a length of suture having two ends; and a distal sheath extending from the foot housing, the distal sheath defining a guidewire lumen;

advancing the suturing device through the inferior vena cava, right atrium, and patent foramen ovate such that the foot is positioned in the left atrium;

deploying the first foot to a deployed position;

orienting the suture device such that a distal portion of tissue of the PFO is received in the pre-formed curve portion of the foot housing advancing the at least one needle through tissue and further into a first needle receptacle; and advancing at least one end of the length of suture through the tissue to suture the PFO, wherein the foot housing further carries a pivotable second foot, the second foot being operatively connected to the foot actuation wire; said method further including:

prior to the advancing at least one end of the length of suture, deploying the second foot to a deployed position; and advancing a second needle through tissue and further into a second needle receptacle; and wherein the advancing of one of the one needle and the second needle is performed in the proximal direction, and the other of the second needle and the one needle is performed in the distal direction.

2. The method according to claim 1, further including:

independently deploying the first foot and the second foot to the respective deployed position.

3. The method according to claim 1, wherein said deploying the first foot is at an angle, relative to the longitudinal axis of the foot housing, different from that of the other foot.

4. The method according to claim 1, further including:
simultaneously deploying the first foot and the second foot to the respective deployed position, wherein the first foot and second foot are substantially aligned along a common longitudinal axis.

5. The method according to claim 1, wherein
the first and second needles each include a hollow portion housing a respective, detachable suture toggle therein, one toggle being disposed on one end of the length of suture and the other toggle being slidable disposed along the length of the suture, said method further including:
after the advancing of the needles through the respective tissue, detaching the one suture toggle from the respective needle, and sliding the other suture toggle along the suture to tension the other suture toggle against the tissue to suture the PFO.

6. The method according to claim 1, wherein,
said suture device includes a locking device configured to cooperate with the length of suture for locking thereof, and
said advancing the at least one end of the length of suture further including engaging the locking element to lockably suture the PFO.

7. The method according to claim 6, wherein,
said locking device includes a locking element one end of the length of suture, and a plurality of beads along a length of the suture, and
said engaging the locking element includes passing one or more of the plurality of beads through the locking element for locking engagement therewith.

8. The method according to claim 6, wherein,
said locking device includes a seal member defining at least one suture aperture sized for sliding receipt of the suture therethrough, said seal member being sized and dimensioned to extend at least partially over and against the proximal side of the sutured PFO;
said engaging the locking element including:
passing the one end and an opposite other end of the length of suture through the at least one suture aperture;
tensioning and locking the seal member along the drawn suture, and against the proximal side of the sutured PFO.

9. The method according to claim 1, wherein
said suturing device includes a flexible filament disposed along the length of the first foot and the second foot, and wherein
said advancing the at least one needle of the suturing device through the one of the tissue further causing a first end of the flexible filament to couple to the one end of the length of suture, and
said advancing a second needle of the suturing device through the tissue further causing the second end of the flexible filament to releasably coupled to the second needle.

10. The method according to claim 9, further including:
retracting the second needle from the second needle receptacle of the deployed second foot, and the tissue, and causing the second end of the flexible filament, coupled to the second needle, to be drawn the tissue.

11. The method according to claim 10, wherein
said advancing at least one end of the length of suture through the tissue is further performed by drawing the flexible filament, coupled to the one end of the length of suture, through the tissue until the one end of the length of suture, coupled to the first end of the flexible filament, is also drawn there through.

12. The method according to claim 1, wherein
said deploying the first foot includes deploying the first foot about a pivotal axis oriented proximate to and distal from a nadir of the pre-formed curved portion of the foot housing.

13. The method according to claim 1, wherein
the deploying the of the first foot and the second foot are such that a length of the deployed first foot from a distal end thereof to the foot housing is longer than that of the second foot.

14. A method for suturing a Patent Foramen Ovale (PFO), the method comprising:
providing a suturing device including a housing having a foot actuation handle and a needle actuation handle, the housing having a proximal end and a distal end; a flexible shaft extending from the distal end of the housing, the flexible shaft having proximal end and a distal end; a foot housing extending from the distal end of the shaft, the foot housing including a pivotable first foot and a second pivotal foot, the first foot and second foot being operative connected to a foot actuation wire, the foot actuation wire being connected to the foot actuation handle; a first needle and a second needle each extending from the needle actuation handle and through the shaft; a length of suture having two ends; and a distal sheath extending from the foot housing, the distal sheath defining a guidewire lumen;
advancing the suturing device through the inferior vena cava, right atrium, and Patent Foramen Ovale (PFO such that the foot is positioned in the left atrium; deploying the first foot and the second foot to a deployed position;
advancing the first needle through tissue and further into a first needle receptacle;
advancing a second needle through tissue and further into a second needle receptacle, wherein the advancing of one of the first needle and the second needle is performed in the proximal direction, and the other of the second needle and the first needle is performed in the distal direction; and
advancing at least one end of the length of suture through the tissue to suture the PFO.

15. The method according to claim 14, wherein
said deploying the first foot is at an angle, relative to the longitudinal axis of the foot housing, different from that of the second foot.

* * * * *